United States Patent [19]

Böhme et al.

[11] Patent Number: 4,580,684
[45] Date of Patent: Apr. 8, 1986

[54] RADIOMETRIC MEASUREMENT

[75] Inventors: Rolf C. Böhme, Kyalami; Max M. Lazerson, Northcliff, both of South Africa

[73] Assignee: General Mining Union Corporation Limited, South Africa

[21] Appl. No.: 481,573

[22] Filed: Apr. 1, 1983

[51] Int. Cl.[4] .............................................. B07C 5/346
[52] U.S. Cl. .................... 209/549; 209/576; 250/394
[58] Field of Search ............... 209/549, 576, 577, 578, 209/589; 250/255, 356.1, 356.2, 358.1, 359.1, 360.1, 428, 433–435, 349, 394

[56] References Cited

U.S. PATENT DOCUMENTS

| | | |
|---|---|---|
| 2,717,693 | 9/1955 | Holmes . |
| 3,025,961 | 3/1962 | Yetterland ........................ 209/576 |
| 3,052,353 | 9/1962 | Pritchett . |
| 3,075,641 | 1/1963 | Hutter et al. . |
| 3,237,765 | 3/1966 | Gaudin et al. . |
| 3,278,747 | 10/1966 | Ohmart ........................... 209/589 X |
| 3,502,876 | 3/1970 | Lasseur .......................... 250/394 X |
| 3,665,188 | 5/1972 | Gutmann ........................ 250/394 X |
| 4,231,478 | 11/1980 | Stone .............................. 209/576 |
| 4,317,521 | 3/1982 | Clark et al. . |
| 4,320,841 | 3/1982 | Gordon et al. ................. 209/589 X |
| 4,361,238 | 11/1982 | Kealy et al. ..................... 209/576 |
| 4,394,907 | 7/1983 | Bohme et al. ................... 209/576 X |

FOREIGN PATENT DOCUMENTS

| | | | |
|---|---|---|---|
| 0229892 | 4/1959 | Australia ........................ 209/576 |
| 0478286 | 11/1951 | Canada .......................... 209/576 |
| 1143276 | 2/1963 | Fed. Rep. of Germany ...... 250/394 |
| 658572 | 10/1951 | United Kingdom . |
| 855678 | 12/1960 | United Kingdom . |
| 939537 | 10/1963 | United Kingdom . |
| 960408 | 6/1964 | United Kingdom . |
| 1030203 | 5/1966 | United Kingdom . |
| 1218844 | 1/1971 | United Kingdom . |
| 1479972 | 7/1977 | United Kingdom . |
| 2046435 | 11/1980 | United Kingdom . |
| 0483928 | 12/1978 | U.S.S.R. ........................ 250/394 |

*Primary Examiner*—Robert B. Reeves
*Assistant Examiner*—Edward M. Wacyra
*Attorney, Agent, or Firm*—Barnes & Thornburg

[57] ABSTRACT

A method of and apparatus for detecting a characteristic in particulate material wherein a stream of the material is caused to move past a plurality of detectors, each of which is responsive to the characteristic, the detectors being so arranged in relation to the material stream that the combined response of the detectors for a given particle possessing the characteristic is substantially independent of the position of the particle relative to the detectors as it passes the detectors.

9 Claims, 3 Drawing Figures

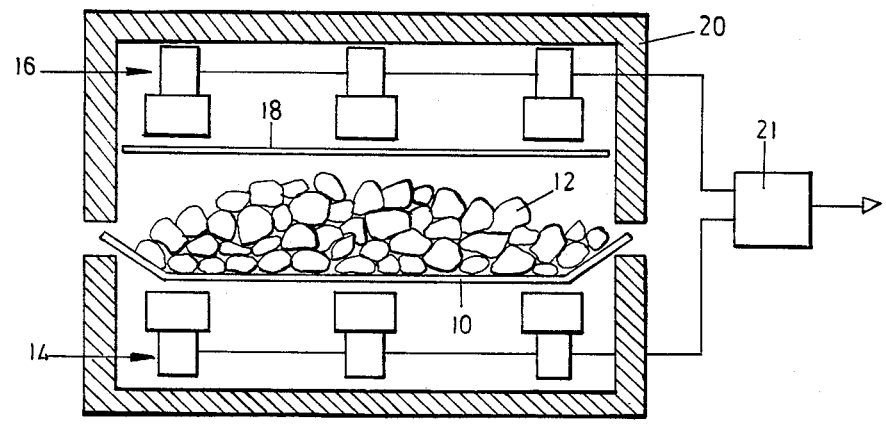
FIG_1
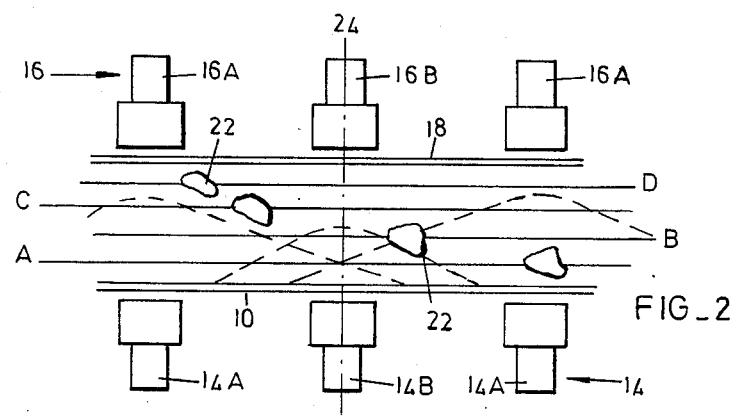
FIG_2
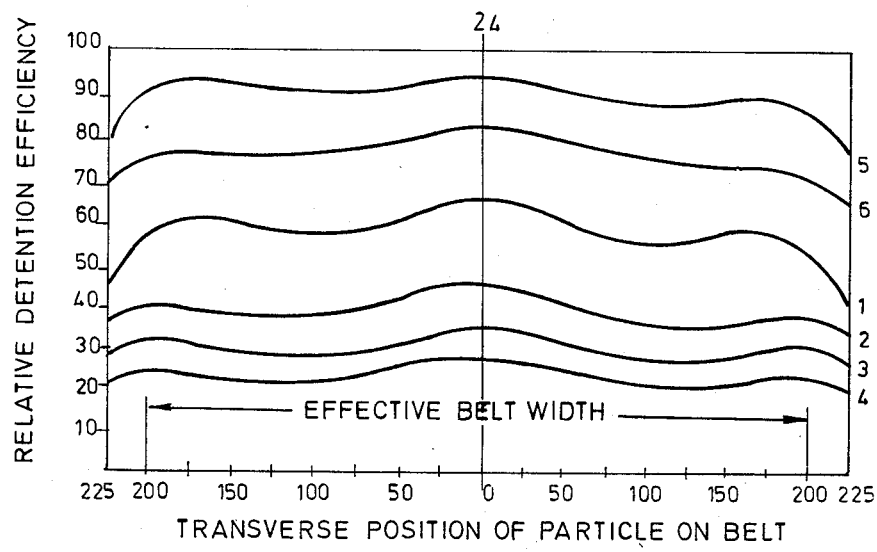
FIG_3

RADIOMETRIC MEASUREMENT

BACKGROUND OF THE INVENTION

This invention relates generally to a method of and apparatus for detecting a characteristic in a stream of particulate material and more particularly to the detection of radioactive material in a stream of material. The invention lends itself to the measurement of grade of radioactive material for example in radioactive ore sorting, in particle or bulk sorting applications and bulk monitoring applications.

In known methods of detecting gamma radiation from radioactive material either single or multiple scintillation detectors have been used, these being mounted under a conveyor belt carrying the material or under the trajectory of material in free flight. These detectors provide a measure of the grade of radioactive mineral content of the material and enable one to sort the material into, accept and reject fractions or to monitor continuously the grade of a bulk stream of the material.

It has also been proposed to pass the material through a ring detector, or among a number of detectors arranged around the material path, as is done for example in U.S. Pat. No. 3,052,353. Other detector arrangements are disclosed in U.S. Pat. Nos. 4,317,521, 3,237,765, 3,075,641, and 2,717,693, and British patent specifications Nos. 1479972, 1218844, 1030203, 960408, 939537, 855678 and 658572. In general these methods have the inherent shortcoming that the detection efficiency varies considerably with the transverse position of a radioactive ore particle in relation to the scintillation detector or detectors and, in bulk sorting applications, the detection efficiency is also dependent upon the vertical position and the distance of a radicactive ore particle in relation to the detectors. This shortcoming manifests itself as an error in the calculation of the grade of a particle or the average grade of a bulk stream and can cause the grade estimation to be in error by a factor of up to five times.

Known particle sorters have used a technique of compensating the apparent grade of the particle by a factor which is dependent on the transverse or lateral position of the particle, relative to the detectors, but this technique is not always accurate and can result in a particle being assigned a grade materially different from its actual grade.

SUMMARY OF THE INVENTION

It is an object of the present invention to provide an improved method of detecting a characteristic in a stream of particulate material.

The invention provides a method of detecting a characteristic in particulate material wherein a stream of the material is caused to move past a plurality of detectors, each of which is responsive to the characteristic, the detectors being so arranged in relation to the material stream that the combined response of the detectors for a given particle possessing the characteristic is substantially independent of the position of the particle relative to the detectors as it passes the detectors.

Thus, in accordance with the invention, the detectors are positioned so that their combined detection efficiency is substantially uniform i.e. is substantially independent of the transverse position, depth or orientation, of the given particle within the stream.

In one form of the invention this is achieved by conveying the material in a stream on a suitable carrier past a plurality of detectors which are arranged at least on two opposed sides of the carrier e.g. above and below the carrier.

The effective width of the carrier may be chosen so that the material stream is within a region where combined detector response is uniform.

The detectors are preferably located in a plane which is at right angles to the dirction of movement of the material stream.

It is for example known from British patent specification, No. 960408 and from the specification of the applicants British patent application No. 2046435A to make use of a ring detector through which the particulate material is passed. Apart from the fact that it is prohibitively expensive to provide a ring detector for a significant bulk flow of radioactive ore a ring detector does not necessarily have a uniform response for a given particle at different positions inside the detector. The ring detector is effective at collecting a high proportion of emitted radiation, and this is desirable when working with low grade ore, but it is equally desirable to have a uniform detector efficiency.

Protective means, e.g. a screen or plate, may be provided below the upper detectors to protect the upper detectors from damage which may be caused by the material stream.

The invention lends itself particularly to the detection of radioactive particles in a stream of ore particles, and may-be applied to particle or bulk sorters, or to bulk monitors.

In radioactive applications of the kind described the detectors are scintillation detectors and, in accordance with the invention, may be housed inside a radioactivity shield. This provides a reduction in the background radiation count.

The invention also provides apparatus for use with particulate material which includes a plurality of detectors each of which is responsive to a characteristic in the material, and means for conveying the material past the detectors which are arranged above and below the conveying means in such a way that the combined response of the detectors for a given particle possessing the characteristic is substantially independent of the position of the particle relative to the detectors as it passes the detectors.

In one form of the invention the detectors are arranged so that they are substantially simultaneously responsive to the characteristic in the given particle. This may be achieved by positioning the detectors in a plane which is substantially at right angles to the direction of movement of the conveying means.

In another form of the invention the detectors are arranged spaced from each other in the direction of movement of the material. The detector responses are combined, for example by simple addition or superimposition of the respective signals which are delayed, or otherwise time compensated, to take into account the speed of movement of the material stream. In this way the combined signal is made time independent, and is dependent only on the strength of the characteristic in the particle.

The combined response characteristic of the detectors may be substantially constant over a central region which contains the conveying means, and may have portions of reducing efficiency or sensitivity on opposed sides of the conveying means.

The principles of the invention lend themselves to incorporation in a sorter and equally in a monitor for quality assurance type surveillance of, for example, a reject fraction in a bulk ore sorter. In such a sorter the accept fraction consists of the ore stream components with a grade above a cut off value. Thus the reject fraction grade lies below the cut off value. Consequently, and bearing in mind that the apparatus of the invention has a response which is independent of particle position, the monitoring of the reject, or alternatively the accept, fraction is readily accomplished by treating the combined uniform response for a given grade as a reference and by equating the reference to the cut off value. Deviation of the measured grade above, or below, the reference value as the case may be then denotes a sorter malfunction and upon the occurrence thereof an appropriate alarm e.g. audible or visual can be initiated.

BRIEF DESCRIPTION OF THE DRAWINGS

The invention is further described by way of example with reference to the accompanying drawings in which:

FIG. 1 is a sectional end view of portion of a system sorting radioactive material in accordance with the invention, FIG. 2 is a schematic sectional side view of the system of FIG. 1, with superimposed detector characteristics, and FIG. 3 shows a series of curves which illustrate the advantages derived from the invention.

DESCRIPTION OF PREFERRED EMBODIMENT

FIG. 1 illustrates a conveyor belt 10 which carries a bulk stream of ore 12 past scintillation detectors 14 positioned below the belt and scintillation detectors 16 positioned above the belt. A protection screen or plate 18 is positioned below the detectors 16 above the stream of ore and protects the detectors against damage which may otherwise be caused to the detectors by the ore particles. A rectangular lead shield 20 surrounds the detectors 14 and 16 and the sandwiched ore stream. The output signals of the detectors are fed to a logic unit 21.

The apparatus of FIG. 1 may operate in a sorting mode in which case the logic unit 21 controls the operation of a gate or other device (not shown) which operates on the stream of ore 12 and separates it into accept and reject fractions. Alternatively the apparatus may function as a bulk ore monitor for a sorter which outputs the ore stream 12 as its reject fraction. The grade of the ore is then monitored and when it exceeds a predetermined value, indicating that the sorter is malfuntioning, the logic unit may initiate an appropriate alarm or suitable corrective action.

The detectors 14 and 16 have predetermined dimensions and are positioned relative to one another and to the ore stream in such a way that the combined response of the detectors to a radioactive particle passing the detectors is substantially independent of the position of the particle in the ore stream. In other words the detectors provide a relatively uniform detection efficiency for any such radioactive particle, the response signal of the detectors being substantially independent of the transverse position, depth or orientation of the radioactive particle in the stream.

FIG. 1 illustrates a bulk stream 12 of ore. Clearly radioactive particles within the stream can be at any position within the bulk of the material and the positioning of the scintillation detectors allows for the detector geometry, the relative position of the particle within the stream and the absorption of radiation from the particle by material below or above the particle.

When the principles of the invention are adapted for use in a particle sorter then the positioning of the scintillation detectors is such as to take into account transverse displacement of the particle and also non-uniform distribution of radioactive material; for example particles which are generally barren material but with a small section of radioactive material on the surface area. Naturally the objectives of the invention are more readily achieved when the stream 12 is of a uniform depth which is predetermined for the detector configuration.

For example FIG. 2 illustrates the detectors 14 and 16, and superimposed on the belt, in dotted outline, the detection characteristics of the three lower detectors. The three upper detectors have similar characteristics, but these have been omitted for the sake of clarity.

Each detector characteristic is substantially a Gaussian curve. In this case the two outer detectors (14A; 16A) are relatively large e.g. with an effective receptor surface of approximately 9 square inches and thus their peak efficiencies are higher than that of the middle detector (14B; 16B) with a receptor surface of approximately 6 square inches. It is found that the combination of two large outer detectors, and a relatively smaller inner detector, suitably spaced from each other, provides a surprisingly uniform combined detection characteristic.

FIG. 1 illustrates a practical case of bulk ore sorting wherein the stream of material has an effective bulk particle width of about 400 mm and a height of about 100 mm. With this configuration three detectors 14 are mounted transversely under the conveyor belt i.e. in a line which is at right angles to the direction of movement of the belt and three detectors 16 are mounted in a line which is directly above the lower line of detectors. The centre to centre spacing and the relative positioning of the detectors are calculated such that the output of the detectors integrated during the movement of a particle through the effective counting zone of the detectors is substantially independent of the transverse position of the particle on or above the belt and is also independent of the particle orientation. The exact positions of the detectors will, however, largely be determined by trial and experiment in an actual installation.

In the first instance therefore the detectors on each side are arranged to give a combined uniform characteristic and, secondly, the positions of the two sets of detectors, on opposing sides of the belt, are varied so that the combined response of both sets of detectors is substantially uniform for a particle irrespective of the position of the particle between the two sets of detectors.

In addition the width of the belt is configured so that the ore stream lies within the central region of uniform response of the detectors and does not encroach on the end regions of the response curve where a reduction in the response efficiency takes place. FIG. 2 illustrates particles 22 in four different planes A, B, C, and D and at different transverse positions relatively to the centre line 24 of the belt. FIG. 3 illustrates curves 1 to 6 of detection efficiency as a function of transverse position of the particle 22 on the belt, relative to the centre line 24, in each of the planes A to D. The curves 1 to 4 are detection efficiency curves achieved with a conventional detector configuration, in this case when use is made of the three detectors only which are of the same size and which are mounted below the belt. The curves 1 to 4 are generally of the same shape but the highest detection efficiency (curve 1) is achieved when the particle 22 is in the lowermost plane A which is closest to the detectors. When the particle 22 is in the plane D which is furthest from the detectors the detection efficiency is at its lowest (curve 4). The relative detection efficiency for the conventional detector configuration varies for the planes A to D, for a particle on the centre line 24, over the range of from 65% to 20% i.e. by a ratio of 3:25:1.

The curves 5 and 6 illustrate the relative detection efficiency when use is made of suitable configurations of detectors 14 and 16, of the kind described in connection with FIG. 1, positioned below and above the belt 10 respectively. The curve 5 gives the detection efficiency for the particle 22 in the plane A or D while the curve 6 is a similar curve for the particle in plane B or C. With this detector configuration it can be seen that the relative detector efficiency varies over the range from 95% to 70% i.e. by a ratio of 1:35:1.

It follows that the detector configuration shown in FIG. 1 and in FIG. 2 gives a more accurate determination of the grade of individual particles of radioactive material in the stream and hence gives better defined sorting characteristics in the case of a particle or bulk sorter and, in the case of a bulk monitor, gives more accurate average grade measurements.

We claim:

1. A method of detecting a characteristic in particulate material wherein a stream of the material is caused to move past a plurality of at least six detectors, each of which is responsive to the characteristic, the detectors being arranged transversely with at least three detectors above the material stream and at least three detectors below the material stream and arranged so that in each case at least two relatively large detectors are on opposing sides of at least one inner relatively smaller detector so that the combined response of the detectors for a given particle possessing the characteristic is substantially independent of the position of the particle relative to the detectors as it passes the detectors.

2. A method of monitoring the operation of a bulk ore sorter in which the reject fraction of the ore sorter is monitored using the method of claim 1 the reject fraction forming the said stream of material, and wherein an alarm condition is initiated when the combined detector response exceeds a predetermined reference value.

3. Apparatus for use with particulate material which includes a plurality of at least six detectors each of which is responsive to a characteristic in the material, and means for conveying the material past the detectors which are arranged transversely with at least three detectors above the conveying means and with at least three detectors below the conveying means and arranged so that in each case at least two relatively large detectors are on opposing sides of at least one inner relatively smaller detector so that the combined response of the detectors for a given particle possessing the characteristic is substantially independent of the position of the particle relative to the detectors as it passes the detectors.

4. Apparatus according to claim 3 in which the detectors are substantially simultaneously responsive to the characteristic in the given particle.

5. Apparatus according to claim 3 wherein the detectors and at least portion of the conveying means are located inside a shield.

6. Apparatus according to claim 3 in which the width of the conveying means is such that the material on the conveying means lies within a region wherein the combined detector response is uniform, the combined detector response efficiency decreasing outside the region.

7. An ore sorter which includes apparatus according to claim 3 and which includes a logic unit to which the combined detector response is applied which controls means for separating the ore stream into accept and reject fractions.

8. A monitor which includes apparatus according to claim 3 and which includes a logic unit to which the combined detector response is applied which initiates an alarm condition when the combined detector response exceeds a predetermined value.

9. Apparatus for use with particulate material which includes six detectors, each of which is responsive to a characteristic in the material, and means for conveying the material past the detectors which are arranged transversely with three detectors above the conveying means, and three detectors below the conveying means, arranged so that in each case two relatively large detectors are on opposed sides of an inner relatively smaller detector.

* * * * *